(12) United States Patent
Caers et al.

(10) Patent No.: US 7,935,851 B2
(45) Date of Patent: May 3, 2011

(54) ISOBUTYLENE

(75) Inventors: Raphael Frans Caers, Edegeon (BE); Eddy Theophile Van Driessche, Ecklo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 1033 days.

(21) Appl. No.: 10/571,653

(22) PCT Filed: Sep. 17, 2004

(86) PCT No.: PCT/EP2004/010621
§ 371 (c)(1), (2), (4) Date: Oct. 31, 2006

(87) PCT Pub. No.: WO2005/028404
PCT Pub. Date: Mar. 31, 2005

(65) Prior Publication Data
US 2007/0106102 A1  May 10, 2007

(30) Foreign Application Priority Data
Sep. 23, 2003  (GB) .................................. 0322246.0

(51) Int. Cl.
C07C 45/50 (2006.01)
C07C 29/14 (2006.01)
C07C 51/16 (2006.01)

(52) U.S. Cl. ..................... 568/454; 568/880; 562/538

(58) Field of Classification Search ............... 568/454, 568/880; 562/538
See application file for complete search history.

(56) References Cited

U.S. PATENT DOCUMENTS

| 3,979,474 A | 9/1976 | Zerrweck |
| 4,287,370 A | 9/1981 | Harris et al. |
| 4,391,677 A | 7/1983 | Harris et al. |
| 4,668,651 A | 5/1987 | Billig et al. |
| 4,769,498 A | 9/1988 | Billig et al. |
| 5,288,918 A | 2/1994 | Maher et al. |
| 5,364,950 A | 11/1994 | Babin et al. |
| 6,100,432 A | 8/2000 | Borgel et al. |
| 6,555,716 B2 | 4/2003 | Protzmann et al. |
| 2003/0022947 A1 | 1/2003 | McAtee et al. |

OTHER PUBLICATIONS

Kirk-Othmer, Encyclopedia of Chemical Technology, $4^{th}$ edition, vol. 17, John Wiley & Sons, 1996; pp. 902-919, "Oxo Process" by E. Billig and D.R. Bryant, Union Carbide Corporation; p. 903, last two lines, referring to A.A.Oswald et al. a presentation at the Lubrizol Award Symposium of the 1982 Spring ACS Meeting, Las Vegas.

Chemiker Zeitung, *Hydroformylierung Von Butenen Unds Pentenen—Synthesen, Produkte Und Möeglichkeiten Ihres Einsatzes* by Von Walter J. Scheidmeir; vol./Issue 96/7; pp. 383-387.

*Primary Examiner* — Sikarl A Witherspoon
(74) *Attorney, Agent, or Firm* — Andrew B. Griffis; Leandro Arechederra, III

(57) ABSTRACT

High purity isobutylene streams are obtained by the hydroformylation of mixed butene streams containing butene-1 and isobutylene (and optionally butene-2) under conditions that hydroformylate primarily butene-1 to yield a mixture of valeraldehyde and isobutylene, which may be separated out as an enriched isobutylene stream and used in the production of methyl tertiary butyl ether, tertiary butyl alcohol, di-isobutylene or polyisobutylene.

12 Claims, 5 Drawing Sheets

ISOBUTYLENE

CROSS REFERENCE TO RELATED APPLICATIONS

This application is a national stage filing of International Patent Cooperation Treaty Application No. PCT/EP2004/010621 filed Sep. 17, 2004, the disclosure of which is fully incorporated herein by reference.

FIELD OF INVENTION

The present invention relates to isobutylene and the production and use of enriched isobutylene streams.

BACKGROUND

Isobutylene is a useful chemical raw material that is used in the manufacture of products such as methyl tertiary butyl ether and/or ethyl tertiary butyl ether, which are used as gasoline components; polyisobutylene that is used as a rubber and as an adhesion promoter as well as in the production of dispersants used in lubricating oils; and di-isobutylene that is used as an intermediate for surfactants and carboxylic acids. Isobutylene is also used as a raw material in the production of tertiary butyl alcohol.

Isobutylene is generally present as a component in the $C_4$ cuts that are obtained from steam cracking and catalytic cracking refinery processes. These cuts typically contain a mixture of $C_4$ saturated materials, particularly isobutane and normal butane, and $C_4$ unsaturated materials including butadiene, normal butenes including both butene-1 and butene-2 and isobutylene. The butadiene may be removed by extraction or reaction, or converted by selective hydrogenation to produce a stream which contains predominantly normal butenes, isobutylene (or isobutene), and butanes; such a stream is sometimes known as raffinate-1. The isobutylene content of a stream may be determined by using conventional gas chromatographic techniques.

Butene streams are used as raw materials for hydroformylation to produce valeraldehyde. The valeraldehyde may then be dimerised and the product of dimerisation hydrogenated to produce 2 propyl heptanol or mixtures thereof with other alcohols which are finding use as alcohols in esterification reactions to produce plasticiser esters. Alternatively valeraldehyde may be hydrogenated to produce pentanol or amyl alcohol or mixtures of different isomers thereof which may be used as a solvent or in the production of zinc dialkyl dithiophosphates. The valeraldehyde may also be oxidised to produce valeric acid or isomer mixtures thereof which may be used in synthetic ester lubricant production. However, in order to obtain these products it is important that the alcohol produced in the hydroformylation reaction is 1 and/or 2 valeraldehyde,

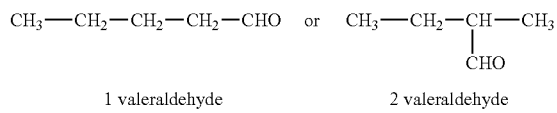

1 valeraldehyde    2 valeraldehyde which are obtained by the hydroformylation of butene-1 or butene-2. It has been preferred that the product is substantially free of 3-methylbutanal, which is the primary product obtained by the hydroformylation of isobutylene, and which is extremely difficult to separate from the other valeraldehydes, especially from 2-valeraldehyde. As is described in U.S. Pat. No. 4,287,370 the presence of isobutylene in hydroformylation reactions can also lead to the formation of undesirable resins.

Hydroformylation reactions of lower olefins such as ethylene, propylene and butenes have generally employed rhodium catalyst stabilised by phosphorus containing ligands operated in what is known as the low pressure oxo technology originally developed by Union Carbide Corporation and currently available under licence from Davy Process Technology Ltd. In another hydroformylation technology, cobalt containing catalysts are used and the process is operated at higher pressures. Exceptionally, rhodium catalyst is also used in high pressure processes, typically without the phosphorus ligand or with only a weak kind of ligand. When using high pressure technologies to hydroformylate mixed butene streams all the unsaturated materials are reacted leading to the presence of undesirable aldehydes and resins from the isobutylene. Generally when using rhodium based low pressure technology to hydroformylate butenes, it has been common practice to separate the isobutylene from the normal butenes in the raffinate-1 to produce a stream containing only n-butenes (butene-1 and butene-2, cis and trans) which can be used for hydroformylation. Such a stream is sometimes known as raffinate-2. The separation of isobutylene from raffinate-1 is however not an easy process and is expensive and time consuming. If fractionation is used a mixture of butene-1 and isobutene tends to be obtained overhead because butene-1 and isobutylene are difficult to separate, whilst the butene-2 tends to be obtained at the bottom of the fractionation tower because it is more easily separated from isobutylene and butene-1. Clearly this is not beneficial if one wants to obtain a butene-1 stream that is substantially free of isobutylene. Accordingly superfractionation may be used; however, this has very high energy requirements and is expensive to operate and complex to design. Furthermore, even the use of superfractionation may not result in complete separation of the isobutylene.

U.S. Pat. No. 6,100,432 shows the separation of isobutylene from raffinate-1 to produce raffinate-2 prior to hydroformylation with a rhodium catalyst. U.S. Pat. No. 4,287,370 states that the $C_4$ feed to hydroformylation should contain no more than 1 wt % isobutylene. Similarly United States Patent Publication 2003/0022947 A1 discloses hydroformylation of raffinate-2, an isobutene depleted stream said to contain no more than 5 mol % isobutene. In this patent only the butene-1 is hydroformylated, the butene-2 and the isobutylene being substantially unreacted. An article by Walter J Scheidmeir of BASF in Chemiker-Zeitung 96 Jahrgang (1972) Nr 7. pp 383-387 shows the hydroformylation of a butene stream containing isobutylene in which all the unsaturated materials including the isobutylene, are converted. U.S. Pat. No. 6,555,716 describes a process in which olefins including raffinate-1 are fed to a tubular hydroformylation reactor which employs a rhodium catalyst in combination with a water soluble ligand, i.e. trisulphonated triphenylphosphine. In this process, high catalyst recycle volumes are required and a higher pressure is employed. In the process of U.S. Pat. No. 6,555,716 butene-1 is selectively hydroformylated whereas butene-2 remains unconverted and isobutylene is partially converted. The examples of U.S. Pat. No. 6,555,716 show that the ratio of the conversion of butene-1 and isobutylene is such that the hydroformylation does not effectively separate butene-1 and isobutylene.

SUMMARY

We have now found that under certain conditions an unsaturated $C_4$ feed containing butene-1 and at least 15 wt % isobutene may be hydroformylated in a manner such that at least 65% of the butene-1 is converted in the hydroformylation reaction and wherein no more than 5% of the isobutylene is converted. This therefore provides a simple technique for the production of a mixture that may be easily separated to produce:

i) $C_5$ aldehydes and alcohols
ii) an enriched isobutylene stream both of which may be subsequently processed as previously described.

The operation of this process avoids the need for the complicated and expensive separation of isobutylene from the unsaturated $C_4$ feed such as raffinate-1.

DETAILED DESCRIPTION

Figure 1:
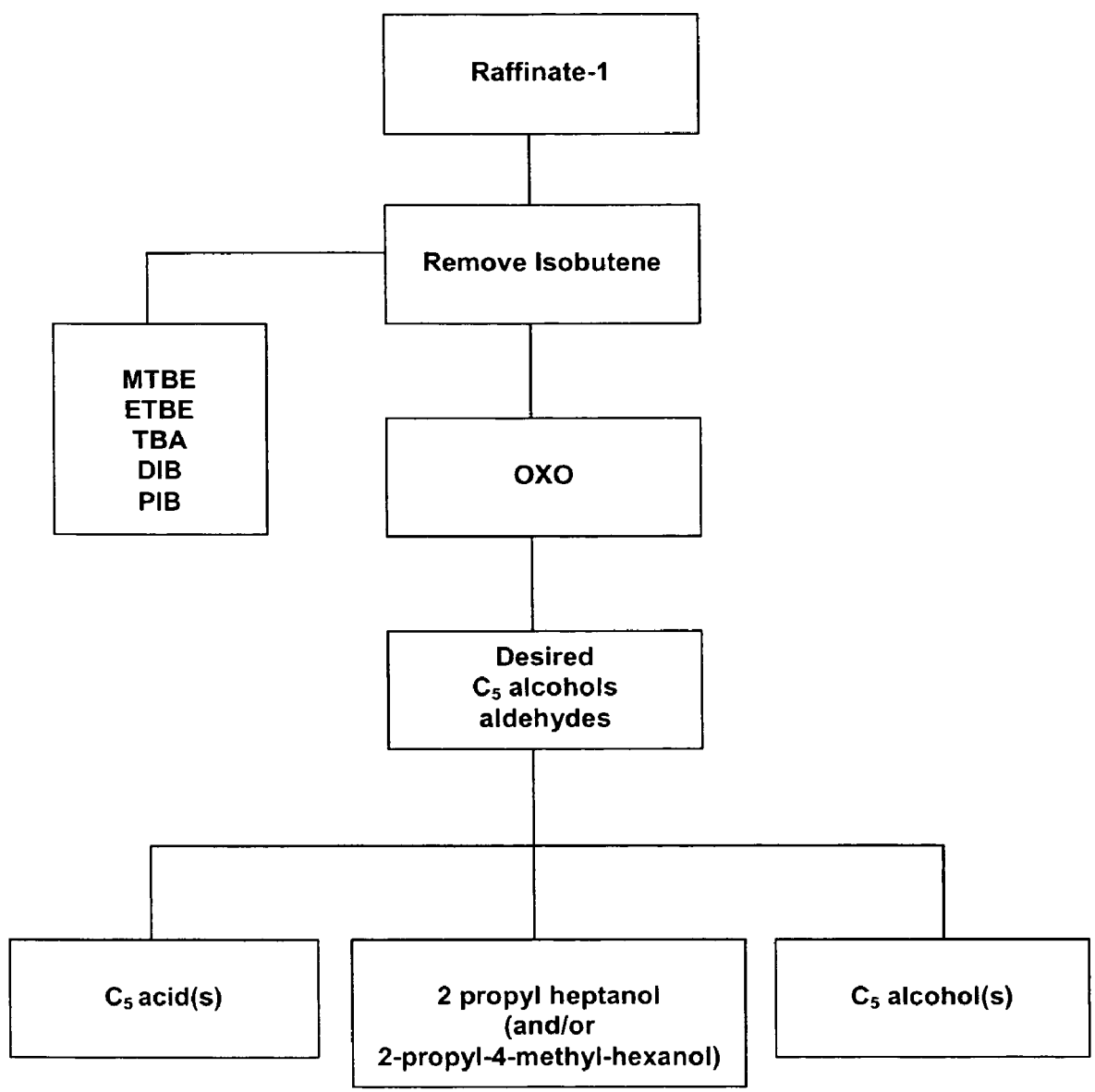
FIG. 1 illustrates the conventional process in which isobutylene is removed prior to hydroformylation.
Figure 2:
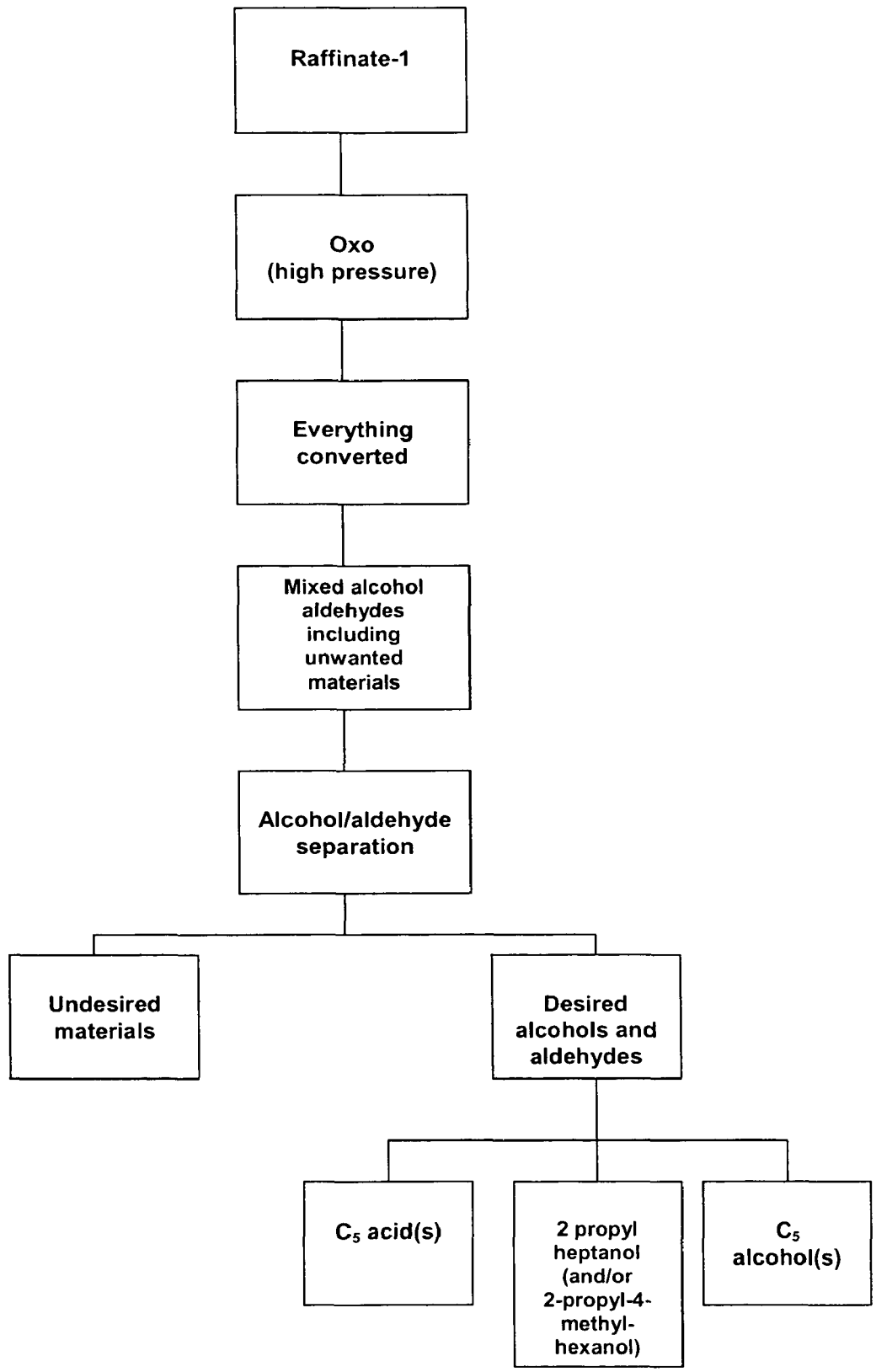
FIG. 2 illustrates the previously proposed process in which all of the unsaturated $C_4$ materials are converted during hydroformylation.
Figure 3:
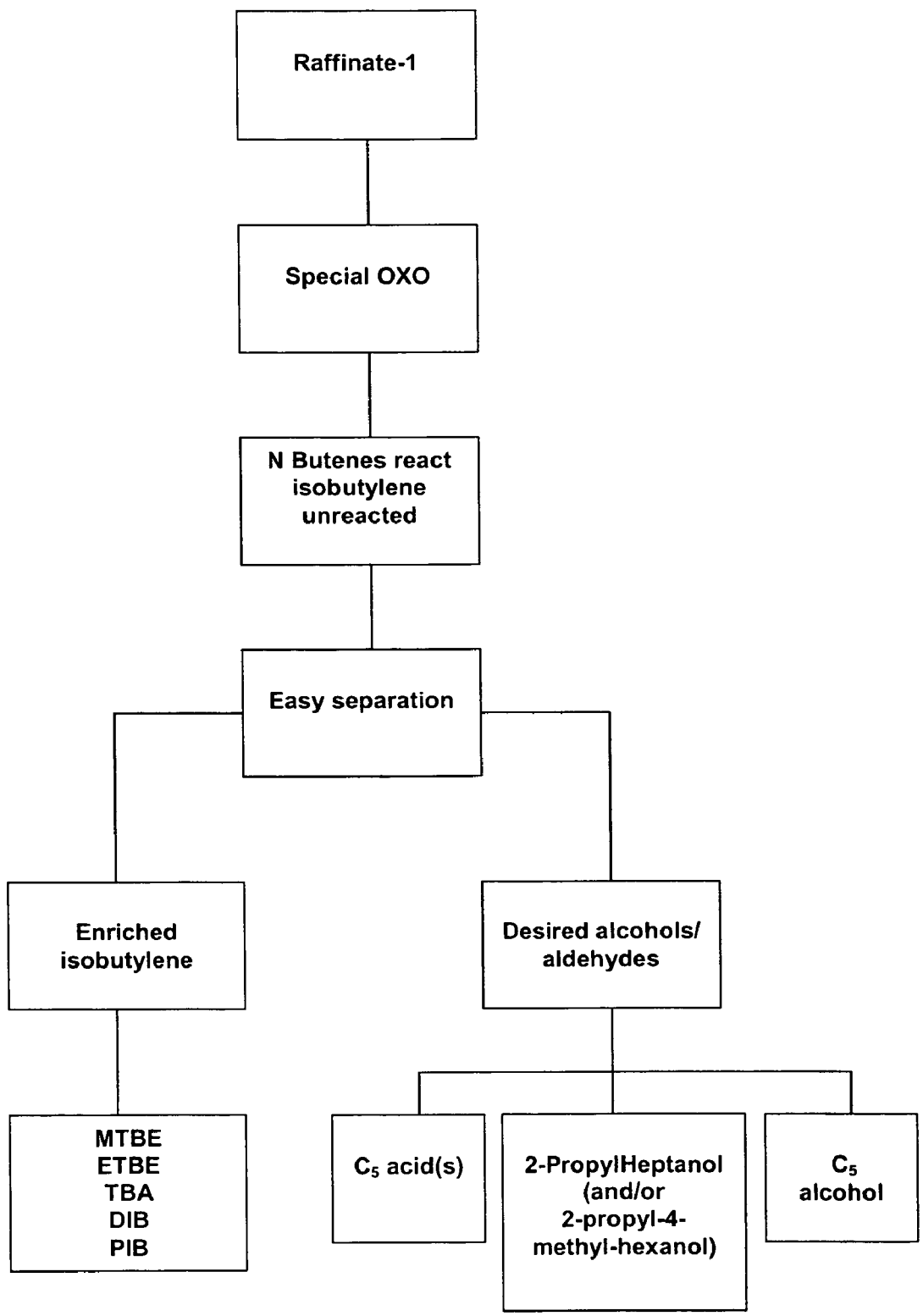
FIG. 3 illustrates the process of the present invention.
Figure 4:
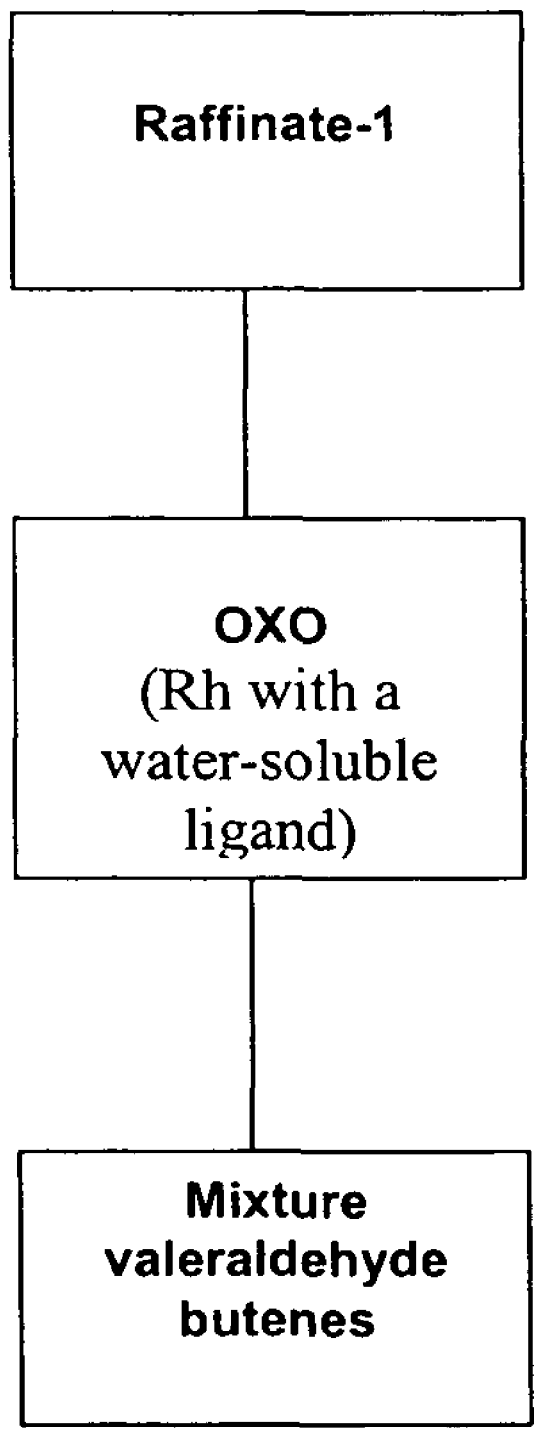
FIG. 4 illustrates the process of Example 13 of U.S. Pat. No. 6,555,716.

The present invention is illustrated by reference to the accompanying drawings which are block diagrams illustrating the previous technologies used with a raffinate-1 $C_4$ refinery feed and the technology of the present invention.

The present invention therefore provides a process comprising:

i) feeding a $C_4$ stream containing butene-1 and at least 15 wt % isobutylene to a hydroformylation reactor;
ii) hydroformylating the $C_4$ feed under conditions that converts at least 65% of the butene-1 and converts no more than 5% of the isobutylene to produce a mixture containing valeraldehyde and/or pentanol and isobutylene; and
iii) separating the valeraldehyde and/or pentanol from the isobutylene.

In an extension of the present invention the valeraldehyde and/or pentanol, isomer mixtures thereof or mixtures of aldehydes and alcohol, are converted into 2-propyl heptanol and possibly 2-propyl-4-methyl hexanol or mixtures thereof with other alcohols preferably by aldol condensation followed by hydrogenation. In another extension the valeraldehyde or valeraldehyde mixture is hydrogenated to pentanol or pentanol mixtures or oxidised to pentanoic acid or mixtures of pentanoic acids. In a further extension of the present invention the isobutylene that is obtained is purified and converted into methyl tertiary butyl ether and/or ethyl tertiary butyl ether, tertiary butyl alcohol, di-isobutylene or polyisobutylene.

The product of the hydroformylation reaction will generally require additional purification. Rhodium catalysed hydroformylation is preferred and typically the reaction products are taken from the reactor as vapour and then condensed although in some systems they can also be taken off as liquid which is subjected to a subsequent flash. The vapours obtained may then be split into the paraffins, the aldehydes, the olefins, unreacted feeds including carbon monoxide and hydrogen which can be recycled, and the heavies, the olefins and the aldehydes being the products of the process of the present invention.

The $C_4$ streams that are used in the present invention contain more than 15 wt % isobutylene and are conveniently those obtained in the steam cracking or catalytic cracking of petroleum feedstocks. The composition of the streams will depend upon the composition of the petroleum feedstock and the conditions employed in the steam cracking or catalytic cracking operation. Typically such feeds contain from 15 to 50 wt % isobutylene and from 40 to 85 wt % normal butenes, any remainder being primarily n-butane and isobutane. More typically the feeds contain from 18 to 45 wt % isobutylene. The normal butenes are generally a mixture of butene-1 and butene-2 (cis- and trans-form) and the relative proportions of those materials will also depend upon the composition of the petroleum feed and the conditions employed in the steam cracking or catalytic cracking operation and the subsequent process steps. A preferred feed however contains from 12% to 30% of butene-1 and from 17% to 40% of butene-2. Other materials such as $C_3$ and $C_5$ hydrocarbons and trace quantities of butadienes and/or $C_4$-acetylenes may be present in the $C_4$ stream.

The $C_4$ stream may contain components that are poisons to the rhodium catalyst or which inhibit the hydroformylation reaction, examples being certain sulphur or chlorine species. To the extent that their presence is undesired, they may be removed or their content reduced by techniques known in the art.

The preferred hydroformylation conditions that are employed convert substantially at least 65% of the butene-1 and preferably all the butene-1 during the hydroformylation reaction and substantially all the isobutylene remains unconverted. We prefer to use rhodium catalysed hydroformylation in a single liquid phase and at low pressures.

The butene hydroformylation is preferably carried out in the presence of a rhodium catalyst complex in conjunction with an organophosphorus ligand. This organophosphorus ligand may be for example a tertiary organophosphine or an organophosphite. The triorganophosphine ligand can be a trialkylphosphine such as tributylphosphine, a $C_1$-$C_6$ alkyldiarylphosphine such as butyldiphenylphosphine, an aryldialkylphosphine such as phenyl-dibutylphosphine, an aryldialkyl diphosphine such as cyclohexyldiphenyl phosphine, tetraphenyldiphosphino-methane, 1,2-bis(diphenyl phosphino) ethane, 1,3-bis(diphenyl phosphino) propane, 1,4-bis (diphenyl phosphino) butane, and the bisphosphine ligands described in EP-A 279,018, EP-A 311,619, WO 90/06810 and EP-A 71,281. However particular phosphines such as triphenylphosphine, tri-p-tolylphosphine, trinaphthylphosphine, phenyldinaphthylphosphine, diphenylnaphthylphosphine, tri(p-methoxyphenyl)phosphine, tri(p-cyanophenyl) phosphine, tri(p-nitrophenyl)phosphine, p-N,N-dimethylaminophenylbisphenyl-phosphine and the like are preferred. Triphenylphosphine (TPP) is most preferred.

Organophosphite ligands can be those disclosed in U.S. Pat. No. 4,599,206, U.S. Pat. No. 4,668,651, U.S. Pat. No. 4,737,588, U.S. Pat. No. 4,748,261, U.S. Pat. No. 4,769,498, U.S. Pat. No. 4,774,361, U.S. Pat. No. 4,789,753, U.S. Pat. No. 4,835,299, U.S. Pat. No. 4,871,880, U.S. Pat. No. 4,885,401, U.S. Pat. No. 5,179,055, U.S. Pat. No. 5,288,918, U.S. Pat. No. 5,312,996, U.S. Pat. No. 5,364,950, U.S. Pat. No. 5,681,473, U.S. Pat. No. 5,756,855, WO 97/20793. Preferred is 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin, or 6,6'-[[3,3',5,5'-tetrakis(1,1-dimethylpropyl)-1,1'-biphenyl-2,2'-diyl]bis(oxy)]bis-dibenzo[d,f][1,3,2]-dioxaphosphepin, or 6,6'-[[3,3'-bis(1,1-dimethylethyl)-5,5'-dimethoxy [1,1'-biphenyl]-2,2'-diyl]bis(oxy)]bis-dibenzo[d,f][1,3,2]-dioxaphosphepin, or tris(2,4,6-di-t-butylphenyl)-phosphite.

Most preferred is 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin. Ionic varieties of such phosphites are disclosed in U.S. Pat. No. 5,059,710 and U.S. Pat. No. 5,113,022.

The hydroformylation process may be carried out in a manner known by the persons skilled in the art, for example by the process according to U.S. Pat. No. 4,247,486, U.S. Pat. No. 4,287,370, U.S. Pat. No. 5,053,551, U.S. Pat. No. 6,100,432, WO 02/00582, DE 10128325, WO 97/20792, WO 97/20793, WO 97/20794, WO 97/20795, WO 97/20796, WO 97/20797, WO 97/20798, WO 97/20799, WO 97/20800 and WO 97/20801. Further variations and improvements on ligands, the hydroformylation process and/or the treatment of the hydroformylation medium have been disclosed in U.S. Pat. No. 5,731,472, U.S. Pat. No. 5,741,942, U.S. Pat. No. 5,741,943, U.S. Pat. No. 5,741,945, U.S. Pat. No. 5,786,517, U.S. Pat. No. 5,763,670, U.S. Pat. No. 5,763,671, U.S. Pat. No. 5,763,677, U.S. Pat. No. 5,763,679, U.S. Pat. No. 5,763,680, U.S. Pat. No. 5,767,321, U.S. Pat. No. 5,789,625, U.S. Pat. No. 5,728,893, U.S. Pat. No. 5,886,237, U.S. Pat. No. 5,741,944, U.S. Pat. No. 5,731,473, U.S. Pat. No. 5,744,650, U.S. Pat. No. 5,874,639, U.S. Pat. No. 5,874,640, U.S. Pat. No. 5,892,119, U.S. Pat. No. 5,886,235, U.S. Pat. No. 5,917,095, U.S. Pat. No. 5,952,530, U.S. Pat. No. 6,090,987, U.S. Pat. No. 6,252,121, U.S. Pat. No. 6,307,109, and U.S. Pat. No. 6,294,700.

Examples of typical C4 feeds to which the present invention may be applied are shown in Table 1.

TABLE 1

C4 feeds containing isobutylene

| | Typical comp. | | |
|---|---|---|---|
| | FCC | Steamcracker Crude C4's Wt % | |
| | C4 cut | After BD extraction | After Sel. Hydro |
| Stream ID | F1 | F2 | F3 |
| Isobutylene | 22 | 47 | 29 |
| Butene-1 | 14 | 25 | 29 |
| Butene-2 cis | 12 | 8 | 10 |
| Butene-2 trans | 17 | 10 | 24 |
| n-Butane | 7 | 8 | 7 |
| Isobutane | 24 | 1 | 1 |
| | 96 | 99 | 100 |
| Remainder | C3-5s, BD | BD | — |

FCC = Fluid Catalytic Cracking
BD = Butadiene
Sel. Hydro = Selective Hydrogenation The butene hydroformylation is preferably carried out under conditions under which the reaction of 1-butene occurs quickly while the 2-butene reacts more slowly, if at all, and the isobutylene remains substantially unreacted. In this way it is possible for butene-1 to be hydroformylated and some butene-2 may be isomerised to butene-1 and then be hydroformylated to produce 1-valeraldehyde while the isobutene and the remainder of the butene-2s present are recovered essentially unchanged. This gives after separation from the valeraldehyde an enriched isobutylene stream that is at the same time low in butene-1. If desired the isobutylene and the residual butene-2 may be separated by fractional distillation to give a stream rich in isobutylene which could not be achieved if residual butene-1 was present.

Thus the present invention enables the production of a new isobutylene concentrate, and according to a further aspect of the invention there is provided an isobutylene concentrate comprising:

(a) $\geq$25 wt % isobutylene
(b) $\leq$10 wt % butene-1
(c) from 5 to 40 wt % butanes
based on the total weight of C4 hydrocarbon components in the concentrate.

The concentrate contains no more than 10% by weight of butene-1, e.g. 0.1 to 10 wt % butene-1, preferably less than 5% of butene-1, more preferably less than 3% butene-1, and most preferably less than 2% by weight of butene-1. The isobutylene content will generally be in the range of from 25% to 90%, e.g. 25% to 75%, preferably at least 30% by weight, more preferably at least 50%, even more preferably at least 60%, and most preferably at least 70% by weight isobutylene. The concentrate will also contain a minor amount of butanes, i.e. n-butane and/or isobutane. The butane content will generally be in the range of 5 to 50% by weight, preferably from 6 to 25%, more preferably from 6 to 15%, even more preferably from 7 to 13%, most preferably from 8 to 12% by weight. Most of the remainder, if any, will be composed of remaining butene-2, generally a mixture of cis-butene-2 and trans-butene-2 unless that has been separated by fractional distillation. The unique combination of low butene-1 content and high isobutylene content makes such concentrates beneficial in their use, because they will improve the yield and efficiency of subsequent processes in which the isobutylene is a raw material.

Under the circumstances that there is no value for any of the isobutylene derivatives at the location of its production, the isobutylene concentrate may be used in more conventional ways for using C4 hydrocarbons. These include their use or recycle as steamcracker furnace feed or catalytic cracker feed to produce more ethylene, propylene and other cracking products or gasoline components, as feed or recycle to a reformer or a partial oxidation or an autothermal reforming unit to produce synthesis gas, which is potentially useful in the hydroformylation step described before, as LPG blendstock, optionally after further hydrogenation treatment, as alkylation feed, either as such or after full or partial saturation, in which case the increased isobutane content is beneficial to the yield and product quality of the alkylation process. After hydrogenation, the resulting butane streams may also be used or sold as such, or after separation of the normal butane from the isobutane, e.g. as specialty solvents or propellants for spray cans or as blowing agents for foam production.

The concentrates discussed above are preferably derived from a steam cracker or catalytic cracker C4 hydrocarbon cut that has been further subjected to low pressure hydroformylation, optionally after butadiene removal or hydrogenation.

In one embodiment of the process of the invention, the preferential hydroformylation of 1-butene over 2-butene and isobutene can be achieved by employing a single liquid phase reaction and preferably with a large excess of triorganophosphorus ligands and by careful control of the temperatures and partial pressures of the reactants and/or products and the length of the reaction. Thus, in this aspect of the present invention the triorganophosphine ligand is preferably used in an amount of at least 100 mol per gram atom of rhodium. The temperature is preferably in the range from 80 to 130° C., the total pressure is preferably not more than 5 MPa and the partial pressure of carbon monoxide is kept below 150 kPa and that of hydrogen is kept in the range from 100 to 800 kPa.

The reaction time can also be varied to control the extent of the conversion of the monomers. For example we have found that when hydroformylating a mixture containing butene-1 and isobutylene using a rhodium triphenylphosphine catalyst at 110° C. and a carbon monoxide partial pressure of about 5 bar, 75% conversion of butene-1 may be achieved with less than 5% isobutylene conversion if the reaction time is less than 1 hour. With higher olefin feed concentrations, the reaction time to reach these conversion differences is expected to be shorter. Also carbon monoxide partial pressure and temperature should affect the reaction time to achieve these conversion differences.

When a phosphite ligand is used the preferred hydroformylation conditions are a total gas pressure (of hydrogen, carbon monoxide and olefinic unsaturated starting compound) of the hydroformylation process ranging from about 0.1 to about 30 MPa. In general, however, it is preferred that the process be operated at a total gas pressure of hydrogen, carbon monoxide and olefinic unsaturated starting compound of less than about 10 MPa, more preferably less than about 3 MPa, most preferably less than about 1.6 MPa. The minimum total pressure is limited predominantly by the amount of reactants necessary to obtain a desired rate of reaction. More specifically the carbon monoxide partial pressure of the hydroformylation process of this invention is preferably from about 0.1 to about 0.8 MPa, and more preferably from about 0.15 to 0.65 MPa, while the hydrogen partial pressure is preferably about 0.1 to about 1.1 MPa and more preferably from about 0.2 to about 0.7 MPa. In general $H_2/CO$ molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150° C. In general, a hydroformylation reaction temperature of about 50° C. to about 120° C. is employed, the more preferred reaction temperatures being from about 50° C. to about 100° C. and most preferably about 80 to 85° C. As with the phosphine ligand system, the reaction time can be varied to control the extent of the conversion. We have found that when using Ligand A (see below) at 95° C. and a carbon monoxide partial pressure of about 5 bar, a 65% conversion of butene-1 with a less than 5% conversion of isobutylene can be achieved with a reaction time of less than 10 minutes. This suggests that similar conversions could be achieved with longer reaction times employing lower carbon monoxide partial pressure and/or a lower temperature.

The hydroformylation with bis-phosphite ligands may be carried out with or without the presence of free ligand. When free ligand is used it is preferred, but not necessary that the free ligand is the same as the ligand of the rhodium-ligand complex catalyst employed. If employed, the amount of free ligand can be as high as 100 moles, or higher, per mole of rhodium metal in the hydroformylation process. Preferably with bis-phosphite ligands the amount of ligand present is from 1 to about 40 moles of bisphosphite ligand per mole of rhodium, more preferably from 1 to 4 moles of bisphosphite ligand per mole of rhodium, said amount of ligand being the sum of both the amount of ligand that is bound (complexed) to the rhodium metal and the amount of free (non-complexed) ligand present. If desired, make-up ligand can be supplied to the reaction medium of the process at any time and in any suitable manner, e.g. to maintain a predetermined level of free ligand in the reaction medium.

Any of these processes may use any suitable solvent. In general, it is preferred to employ as solvents one or more valeraldehydes and/or their liquid condensation by-products that are produced in situ during the hydroformylation process. Rhodium concentrations in the hydroformylation reaction medium may be, for example, in the range from about 10 ppm to about 1000 ppm, calculated as free rhodium. It is generally preferred to operate with from about 10 to 500 ppm of rhodium, and more preferably from 25 to 350 ppm of rhodium.

The catalysts employed in the low pressure oxo hydroformylation reactions are typically rhodium based catalyst that are stabilised by a ligand. Since the advent of rhodium low pressure oxo technology there has been a continuing evolution of the ligands. The most frequently used ligands have been triphenylphosphinic, such as discussed above. Those catalysts employing these ligands would convert primarily butene-1. Accordingly the hydroformylation cycle using rhodium catalyst with such ligands and an isobutylene containing feed has involved:
a) removal of the isobutylene from the feed
b) subjecting the normal butenes to hydroformylation wherein only butene-1 would be converted to valeraldehyde and/or pentanol.
c) separation of the unreacted butene-2 from the valeraldehyde and/or pentanol.

The present invention changes this process in that the isobutylene passes through the hydroformylation reaction substantially unreacted and is then separated from the valeraldehyde and/or pentanol.

More recently bisphosphite ligands, e.g. those of the formula

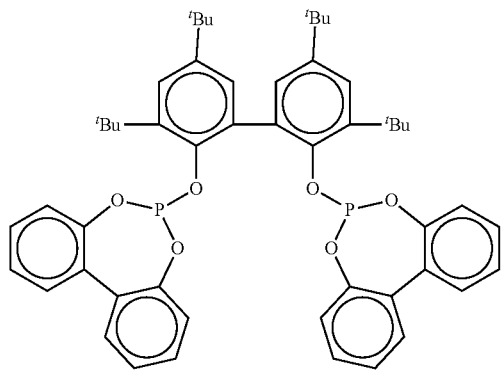

Ligand A have been developed and these are described in U.S. Pat. Nos. 5,364,950, 4,835,299 and 5,288,918. Depending on the conditions employed, the use of catalysts employing those ligands in the hydroformylation of $C_4$ feeds containing normal butenes will convert butene-1 and can also convert a significant portion of the butene-2 to valeraldehyde and/or pentanol.

Accordingly the traditional hydroformylation cycle using these phosphite ligands and an isobutylene containing feed involves:
a) removal of the isobutylene from the feed
b) subjecting the isobutylene free material to hydroformylation to produce valeraldehyde and/or pentanol The present invention changes this process in that the hydroformylation conditions are adapted such that the isobutylene passes through the hydroformylation reaction substantially unreacted and is then separated from the valeraldehyde and/or pentanol.

We have now found however that when catalysts employing these phosphite ligands are used to hydroformylate unsaturated $C_4$ feeds containing isobutylene under standard hydroformylation conditions the isobutylene does not substantially react and so the present invention comprises a hydroformylation cycle comprising:

a) feeding a $C_4$ feed containing butene-1 and at least 15 wt % isobutylene to a hydroformylation reactor
b) subjecting the $C_4$ feed to hydroformylation conditions using a rhodium catalyst with a phosphite ligand whereby at least 65% of the butene-1 is converted to valeraldehyde and/or pentanol and the isobutylene remains unconverted, meaning at least 90%, preferably at least 93%, more preferably at least 95%, most preferably at least 97% of the isobutylene remains unconverted.

In a preferment of this aspect of the invention the isobutylene and the valeraldehyde and/or pentanol are then separated.

As an extension the valeraldehyde and/or pentanol may then be converted to 2-propyl heptanol or mixtures containing 2-propyl heptanol by dimerisation, usually by an aldol reaction, and hydrogenation. As a further extension the enriched isobutylene stream that is obtained by the present invention may be used as a raw material for the production of methyl tertiary butyl ether, ethyl tertiary butyl ether, tertiary butyl alcohol, di-isobutylene, polyisobutylene, or butyl rubber.

Unlike the previous processes involving the difficult separation of isobutylene from other $C_4$ materials, particularly butene-1, isobutylene may be readily separated from valeraldehyde by distillation since their boiling points differ by about 100° C. (−6.9 C vs 92 C/92.5 C/103 C).

According to the invention therefore hydroformylation may be accomplished in a single liquid phase using phosphite ligands or by using phosphine ligands when a large excess of triorganophosphorus ligands is used. The invention may also be accomplished by careful control of the temperatures and partial pressures of the reactants and/or products and the length of the reaction time. Thus, the triorganophosphine ligand is preferably used in an amount of at least 100 mol per gram atom of rhodium. The temperature is preferably in the range from 80 to 130° C., the total pressure is preferably not more than 5000 kPa, the partial pressure of carbon monoxide is preferably kept below 150 kPa and that of hydrogen is preferably kept in the range from 100 to 800 kPa.

The invention therefore provides a substantial improvement in the overall conversion and utilisation of $C_4$ refining streams avoiding the need for hitherto expensive and complex techniques for the separation of isobutylene from $C_4$ refinery streams containing rather moderate concentrations of isobutylene. In addition the invention enables the production of enriched isobutylene streams which can be used as feeds to improve the yield in reactions such as the production of methyl tertiary methyl ether, ethyl tertiary butyl ether, tertiary butyl alcohol, polyisobutylene and di-isobutylene. Some of these isobutylene consuming processes operate chemical reactions of which the reaction rate is higher than first order in isobutylene, and/or operate at relatively low reaction per pass combined with significant recycle of unreacted isobutylene. For reasons of undesired side reactions, some of them use complex steps upfront for further concentration of their isobutylene containing feed streams and/or for rejecting most of the n-butenes, such sections benefiting significantly from a feed stream that is richer in isobutylene.

EXAMPLES

The invention is further illustrated by the following examples, in which the following procedure was employed.

Hydroformylation was carried out in a standard half liter zipperclave reactor from Autoclave Engineers. Mixing occurred with an air driven stirrer with speed controlled at 2000 revolutions per minute. The mixer had a six bladed impeller that guaranteed a strong mixing between the gas and the liquid phase. Baffles inside the reactor prevented vortex formation and created back mixing. The reaction temperature was controlled at 110° C.+/−1° C. Pressure was controlled at 10 barg+/−0.1 bar. Synthesis gas (48% $H_2$ and 52% CO) was delivered from a calibrated high pressure storage cylinder equipped with a pressure transmitter allowing pressure reading at 0.01 bar accuracy.

Each experiment started with a catalyst solution of the following composition:

| | |
|---|---|
| TPP = | 19.84 g |
| Tertraglyme (solvent) = | 191.2 g |
| Rhodium = | 0.00576 g |

The rhodium was dosed using rhodium carbonyl acetylacetonate as catalyst precursor.

The catalyst solution contained 56 wtppm rhodium.

The catalyst solution was transferred into the reactor. The reactor was purged several times with syngas to remove air. The reactor content was then heated up to 110° C. under 2 barg syngas pressure.

Once the desired reaction temperature was reached, about 0.05 mol of olefin was injected in the catalyst solution by means of synthesis gas and at the same time of the substrate injection the pressure was adjusted to 10 barg. Immediately after the olefin injection and pressure adjustment, the progress of the reaction was followed by measuring the rate of gas consumption, indicated by the pressure decay in the high pressure syngas storage cylinder.

The test duration was 3 hours. At the end of the reaction the gas supply was stopped and the reactor was cooled down to room temperature. Then a gas sample was taken from the gas phase inside the reactor and analysed on a HP6890 gas chromatograph equipped with a thermal conductivity detector (TCD) detection system and a poraplot Q column of 30 m length, 0.53 mm internal diameter (ID), 10 micrometer film thickness (df). A liquid sample was then withdrawn from the reactor into a cooled sample vial and analysed for product composition by gas chromatography using a HP6890 gas chromatograph equipped with a flame ionisation detector (FID) detection system and a WCOT Ultimetal column of 10 m*0.53 mm ID, 0.17 micrometer df HPSimdistC. For the determination of dimethylether a second analysis was carried out over a chrompack, CP Wax 52 fused silica of 50 m*0.25 mm ID, 0.2 micrometer df. For the determination of acetaldehyde a second analysis was carried out over a capillary column HP-FFAP polyethyleneglycol TPA (terephthalic acid) of 50 m* 0.32 mm ID, 0.5 micrometer df.

Sulphur analyses of the products were done on a HP6890 gas chromatograph equipped with a fused silica column of 30 m*0.32 ID*5 micrometer CPSIL5CB and a model 355 flameless sulphur chemoluminescence detector from Sievers.

Finally the reactor was depressurized and the liquid recovered and weighed. From the weight of the product, its composition and the composition of the off-gas a substrate molar end-conversion was calculated. The conversion at any given moment could be calculated pro-rata the pressure drop at that moment, the measured end-conversion and the total pressure drop achieved at the end of the experiment.

The results obtained were as follows.

|  | Example 1 | Example 2 | Example 3 |
|---|---|---|---|
| Feed (grams) | | | |
| i-butene |  |  | 2.7 |
| n-butene-1 | 2.7 |  |  |
| n-butene-2 |  | 2.7 |  |
| TPP | 19.84 | 19.84 | 19.84 |
| Rhodium | 0.00576 | 0.00576 | 0.00576 |
| Tetraglyme | 191.2 | 191.2 | 191.2 |
| Product (grams) | | | |
| C4 | 0.124 | 2.24 | 1.97 |
| 3Me butyraldehyde |  |  | 0.45 |
| 2Me butyraldehyde | 0.663 | 0.59 |  |
| n-valeraldehyde | 3.314 | 0.13 | 0.17 |
| Ligand |  |  |  |
| Valeric acid | 0.041 | 0.00 | 0.00 |
| Tetraglyme | 180.985 | 186.16 | 188.62 |
| C4 in offgas | 0.003 | 0.29 | 0.45 |

Example 1

N-Butene-1 Hydroformylation

Conversion was 89%, and the first order initial reaction rate constant as measured was about 3 h-1. A second run (not shown) indicated this to be very reproducible within 10% relative on the rate constant.

Example 2

N-Butene-2 (40% Cis and 60% Trans) Hydroformylation

The conversion after the 3 hours was 14.8%.

Example 3

Iso-Butylene Hydroformylation

The conversion after the 3 hours was 81.7%. It is believed that the trace of n-valeraldehyde in the product originated from a feed impurity.

Comparison of the Three Examples

N-butene-2s and isobutene show at 110° C. and 10 barg a reaction rate of about 0.05 $h^{-1}$ and reacted therefore about 50 times slower than n-butene-1. The main product components are branched valeraldehydes, while only very little n-valeraldehyde is produced.

Figure 5:
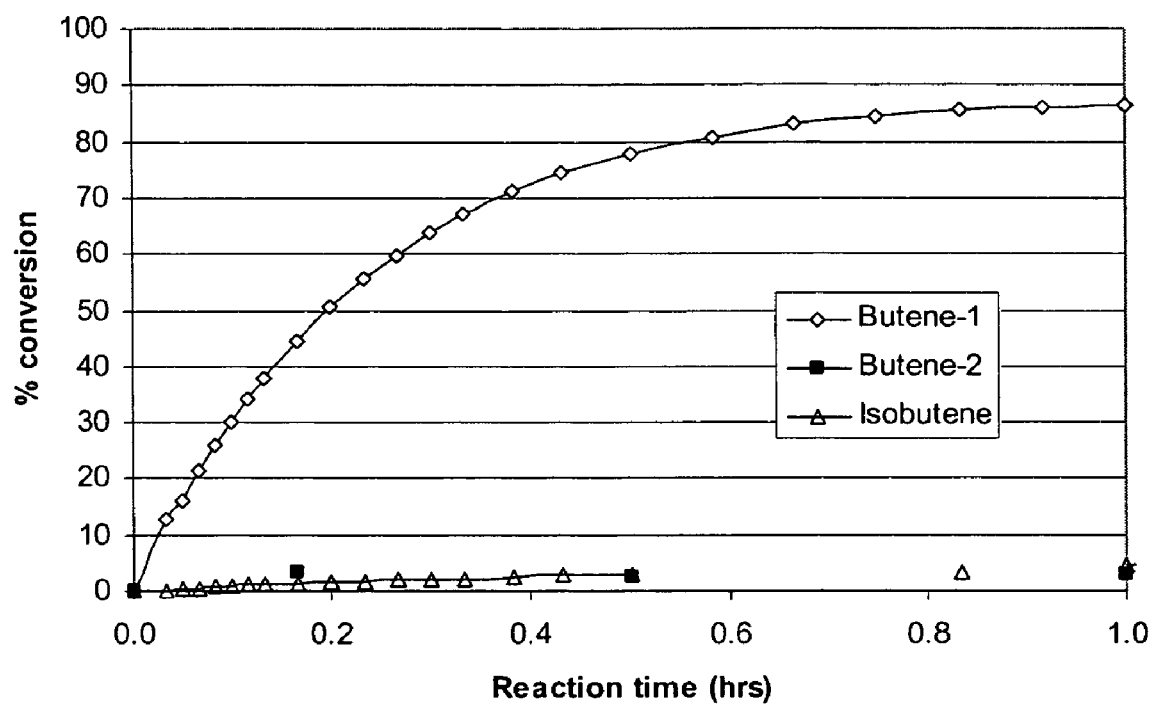
FIG. 5 plots conversion over time for Examples 1-3.

These results show that butene-1 will always react quickly and that by selecting the appropriate conditions (temperature, carbon monoxide partial pressure and residence time), isobutylene can be made not to react, as is illustrated in FIG. 5 which plots the conversions over time achieved in Examples 1, 2 and 3.

The invention claimed is:

1. A process comprising:
   i) feeding a $C_4$ stream comprising butene-1 and at least 15 wt % isobutylene to a hydroformylation reactor,
   ii) hydroformylating the $C_4$ feed under conditions that converts at least 65% of the butene-1 and converts no more than 5% of the isobutylene to produce a hydroformylation mixture comprising isobutylene and a hydroformylation product selected from the group consisting of valeraldehyde, pentanol and mixtures thereof; and
   iii) separating the hydroformylation product from the isobutylene;
   wherein the conditions comprise:
      a) a temperature in the range from 80 to 130° C.;
      b) a total pressure of not more than 5000 kPa;
      c) a partial pressure of carbon monoxide below 150 kPa; and
      d) a partial pressure of hydrogen in the range from 100 to 800 kPa.

2. The process according to claim 1 wherein the hydroformylation product is converted into 2-propyl heptanol by aldol condensation and subsequent hydrogenation.

3. The process according to claim 1 wherein the hydroformulation product comprises valeraldehyde and wherein the process further comprises hydrogenating the valeraldehyde to pentanol and oxidizing the pentanol to pentanoic acid.

4. The process according to claim 1 wherein the hydroformylation is carried out in the presence of a rhodium catalyst.

5. The process according to claim 4 wherein the rhodium catalyst comprises a rhodium complex in conjunction with a triorganophosphorus ligand.

6. The process according to claim 1 which uses rhodium catalyst and a bisphosphite ligand.

7. A process comprising a hydroformylation reaction comprising:
   a) feeding a $C_4$ feed comprising butene-1 and at least 15 wt % isobutylenes to a hydroformylation reactor
   b) subjecting the $C_4$ feed to hydroformylation conditions using a rhodium catalyst with a phosphite ligand whereby at least 65% of the butene-1 is converted to a hydroformylation product selected from the group consisting of valeraldehyde, pentanol and mixtures thereof, and at least 95% of the isobutylene remains unconverted;
   wherein the hydroformylation conditions comprise:
      i) a temperature in the range from 80 to 130° C.;
      ii) a total pressure of not more than 5000 kPa;
      iii) a partial pressure of carbon monoxide below 150 kPa; and
      iv) a partial pressure of hydrogen in the range from 100 to 800 kPa.

8. The process according to claim 7 further comprising separating the hydroformylation product from the isobutylene.

9. The process according to claim 7 further comprising converting the valeraldehyde and/or pentanol to 2-propyl heptanol.

10. A process according to claim 1 further comprising converting the enriched isobutylene separated from the hydroformulation product into a product selected from the group consisting of methyl tertiary butyl ester, tertiary butyl alcohol, di-isobutylene and polyisobutylene.

11. A process according to claim 1 further comprising converting the enriched isobutylene separated from the hydroformulation product into a product selected from the group consisting of synthesis gas, butane, alkylate, LPG, a product of a thermal cracking and a product of catalytic cracking.

12. The process according to claim 1, wherein the conditions comprise a residence time of at least 10 minutes.

* * * * *